(12) United States Patent
Dousono et al.

(10) Patent No.: US 10,357,648 B2
(45) Date of Patent: Jul. 23, 2019

(54) TREATMENT METHOD AND MEDICAL APPLIANCE

(71) Applicant: Terumo Kabushiki Kaisha, Shibuya-ku, Tokyo (JP)

(72) Inventors: Takeshi Dousono, Fujinomiya (JP); Youichi Ito, Fujinomiya (JP); Kikuko Yasuda, Fujinomiya (JP); Takatsugu Yamaguchi, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 411 days.

(21) Appl. No.: 15/425,032

(22) Filed: Feb. 6, 2017

(65) Prior Publication Data

US 2017/0224979 A1     Aug. 10, 2017

(30) Foreign Application Priority Data

Feb. 8, 2016  (JP) ................. 2016-022259

(51) Int. Cl.
*A61N 1/05* (2006.01)
*A61B 1/267* (2006.01)
*A61M 16/04* (2006.01)
*A61N 1/20* (2006.01)

(52) U.S. Cl.
CPC ........... *A61N 1/0519* (2013.01); *A61B 1/267* (2013.01); *A61M 16/0425* (2014.02); *A61N 1/205* (2013.01)

(58) Field of Classification Search
CPC ... A61N 1/0519; A61M 16/0425; A61B 1/267
See application file for complete search history.

(56) References Cited

U.S. PATENT DOCUMENTS

| 4,155,353 A | * | 5/1979 | Rea | ............... A61B 5/04 600/380 |
| 4,351,330 A | * | 9/1982 | Scarberry | ........ A61M 16/04 128/207.15 |
| 5,584,290 A | * | 12/1996 | Brain | ............ A61B 5/0421 128/204.22 |

FOREIGN PATENT DOCUMENTS

JP     2005-253838     9/2005

* cited by examiner

*Primary Examiner* — Christian A Sevilla
(74) *Attorney, Agent, or Firm* — Jason H. Vick; Sheridan Ross, PC

(57) ABSTRACT

A treatment method includes an indwelling step of indwelling a medical appliance in a trachea T of a patient, the medical appliance having a plurality of types of metals disposed side by side on a side surface of a pipe body, and the medical appliance generates a current between adjacent metals out of the plurality of types of metals when in contact with a foreign substance or saliva having flown into the trachea.

20 Claims, 4 Drawing Sheets

TREATMENT METHOD AND MEDICAL APPLIANCE

CROSS REFERENCE TO RELATED APPLICATIONS

The present application claims the benefit of priority, under 35 U.S.C. § 119(e), to Japanese Application No. 2016-022259, filed Feb. 8, 2016, entitled "Treatment Methods and Medical Instruments," the entire disclosure of which is incorporated herein by reference in its entirety, for all it teaches and for all purposes.

TECHNICAL FIELD

The present invention relates to a treatment method and a medical appliance for encouraging coughing.

BACKGROUND

Aspiration pneumonia is a disease that is contracted due to bacteria or the like, adhering to food, saliva, and the like, and as a result of a deficiency in neurotransmitters in the brain to cause reductions in a cough reflex and a swallowing reflex, the entry of the food, the saliva, and the like into the lung through a trachea. The entry of the saliva and the like into the lung without the person noticing as described above is referred to as silent aspiration.

As one of coping techniques for the prevention of the aspiration pneumonia, encouraging the cough reflex is considered to be effective. As a conventional technique for encouraging the cough reflex, there is known a technique for implanting electrodes, to each of which a lead wire is connected, into a trachea of an animal, generating electric pulses in the electrodes, and selectively stimulating the trachea of the animal (see Japanese Patent Application No. JP-A 2005-253838, which is incorporated herein by reference in its entirety for all that it teaches and for all purposes).

SUMMARY OF THE INVENTION

Technical Problem

The technique of the above Japanese Patent Application requires a power supply for the generation of the electric pulses; therefore, the technique is applicable to a patient in hospital but not to a person who is not in hospital. In those circumstances, there is a need of a technique capable of encouraging the cough reflex even without a power supply or the like.

It is, therefore, an objective herein to provide a treatment method and a medical appliance capable of encouraging a cough reflex by generating a current through the inflow of a foreign substance, etc. even without the supply of electric power from a power supply or the like.

Solutions(s) to the Problem(s)

An embodiment of a treatment method includes an indwelling step of indwelling a medical appliance in a trachea of a patient, the medical appliance having a plurality of types of metals disposed on a side surface of a pipe body. The medical appliance generates a current between the adjacent metals out of the plurality of types of metals by a foreign substance or saliva having flown into the trachea.

The medical appliance can include a pipe body that can be indwelled in a trachea of a patient; and a current generation unit having a plurality of types of metals disposed side by side on a side surface of the pipe body and generating a current between the adjacent metals out of the plurality of types of metals by a foreign substance or saliva having flown into the trachea.

Advantages

The operative treatment method and medical appliance may be configured to indwell the medical appliance in the trachea, the medical appliance having a configuration such that a current is generated between the adjacent metals out of the plurality of types of metals by the foreign substance or saliva having flown into the trachea as described above. It is, therefore, possible to generate the current by the foreign substance, saliva or the like having flown into the trachea once the medical appliance has been indwelled in the trachea, while no current is generated when no foreign substance or the like flows into the trachea. As a consequence, it is possible to spontaneously generate an electric stimulus in the trachea and encourage the cough reflex even without lead wires and a power supply, which have been required in the conventional technique.

DETAIL DESCRIPTION

The embodiments herein will be described hereinafter with reference to the accompanying drawings. Note that the disclosure hereinafter is not intended to limit the technical scope and the meanings of terms set forth in claims. Furthermore, the scale of the drawings is exaggerated for the convenience of description and differs from an actual scale.

Figure 1A:
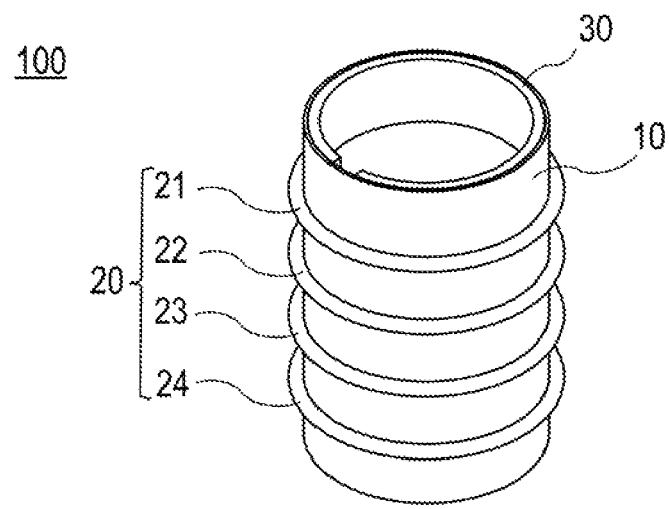
FIGS. 1A to 1C are a perspective view, a front view, and a plan view, respectively, for illustrating an embodiment of a medical appliance.
Figure 1B:
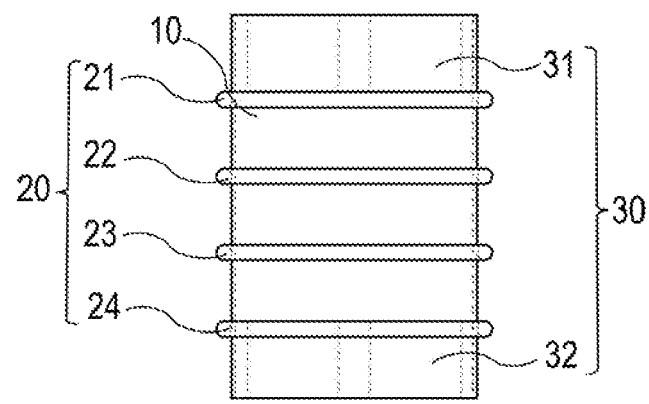
Figure 1C:
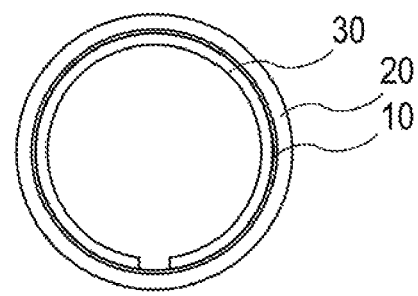
Figure 2:
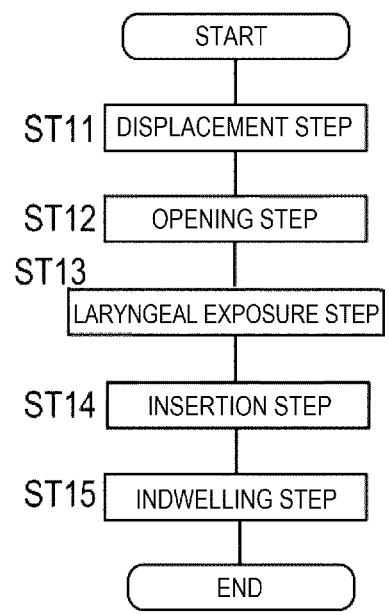
FIG. 2 is a flowchart of a treatment method.

FIGS. 1A to 1C are a perspective view, a front view, and a plan view, respectively for illustrating a medical appliance. FIG. 2 is a flowchart of a treatment method using the medical appliance. FIGS. 3 to 6 are explanatory diagrams for the treatment method.

The treatment method is for encouraging the elimination of a foreign substance by coughing, and indwelling a medical appliance, for the prevention of silent aspiration that may cause pneumonia or the like, in a trachea or the like.

The medical appliance used in the treatment method will first be described. Referring to FIGS. 1A to 1C, a medical appliance 100 will be generally described. The medical appliance 1 includes a pipe body 10 that can be indwelled in a trachea or the like of a patient; a current generation unit 20 which is formed from a plurality of types of metals, the plurality of types of metals being disposed side by side on a side surface of the pipe body 10, and which generates a current between adjacent metals out of the plurality of types of metals by a foreign substance, saliva or the like which has flown into the trachea; and a deformation portion 30 that widens or constricts the pipe body 10 as the trachea widens or constricts. The medical appliance 100 will be now described in more detail.

The pipe body 10 is a member that is indwelled in the trachea and is formed into a generally cylindrical shape similar to a shape of the trachea. The pipe body 10 is formed from a well-known material that could be inserted into a living body, for example, polyurethane, polyvinyl chloride, or silicone rubber.

The current generation unit 20 is disposed on an outer side surface of the pipe body 10 at constant intervals. The current generation unit 20 has metal rings 21, 22, 23, and 24. The metal rings 21, 22, 23, and 24 are obtained by forming two types of metals into a ring shape, and the adjacent metal rings 21 and 22, the adjacent metal rings 22 and 23, and the adjacent metal rings 23 and 24 are formed from different metals. The metal rings 21 to 24 can be configured in such a manner that the metal rings 21 and 23 are formed from a cobalt chrome alloy and the metal rings 22 and 24 are formed from nickel chrome alloy, for example. Alternatively, the current generation unit can be configured in such a manner that the metal rings 21 and 23 are formed from a noble metal and parts corresponding to the metal rings 22 and 24 are formed from a non-metal.

The current generation unit 20, which is configured as described above, thereby generates a galvanic current in response to a stimulus from saliva, a foreign substance or the like. The galvanic current is a current that is generated when different types of metals are electrically connected. The saliva or the like brings the metal rings 21 to 24, disposed at certain intervals, into a state of being electrically connected to one another and the galvanic current is generated, thereby stimulating a cough receptor and generating cough reflex.

Note that the cough reflex is a defensive reflex for eliminating a foreign substance by causing intake air within the lung to suddenly run off against a stimulus within an airway. In this way, the current generation unit 20 generates the current with the saliva or the foreign substance as a trigger and can, therefore, encourage spontaneous cough reflex only when it is necessary to eliminate the foreign substance from the body. Note that the metals, etc. constituting the metal rings 21 to 24 may be other than the abovementioned metals, etc. if the galvanic current can be generated. In that case, the metals, etc. constituting the metal rings 21 to 24 can be combined, as appropriate, in response to the cough sensitivity of the patient to the currents resulting from a potential difference among the different types of metals, etc. Moreover, the metal rings 21 to 24 have been described as disposed at constant intervals in an axial direction of the pipe body 10; however, the disposition is not limited thereto and the metal rings 21 to 24 may be disposed at non-constant intervals as long as the galvanic current can be generated.

Furthermore, the metal rings 21 to 24 are fusion-bonded to the outer side surface of the pipe body 10. However, similarly to the aforementioned, the metal rings 21 to 24 may be bonded to the outer side surface of the pipe body 10 by a method other than fusion bonding as long as the medical appliance 100 can generate the galvanic current and encourage the cough reflex.

The deformation portion 30 is provided to keep a state where the medical appliance 100 is indwelled at a predetermined position in the trachea while the medical appliance 100 is prevented from extremely deviating from the predetermined position in the trachea and from moving to a bronchial tube or the like as the trachea widens or constricts due to respiration or the like. The deformation portion 30 is bonded to an inner wall surface of the pipe body 10 by fusion bonding or the like, and configured as a member having an elastic force that enables widening or constriction in a radial direction of the pipe body 10.

As shown in FIGS. 1B and 1C, the deformation portion 30 is configured such that plate spring 31 and 32 rolled into a circular shape are bonded to the inner wall surface of the pipe body 10 in two portions of an upper end and a lower end of the pipe body 10, respectively, by the fusion bonding or the like. However, the specific configuration of the deformation portion 30 is not limited to the aforementioned if the deformation portion 30 enables the medical appliance 100 to be widened or constricted in the radial direction similarly to the plate springs and to thereby match the shape of the trachea that widens or constricts.

Indwelling the medical appliance 100 in the treatment method will next be described with reference to FIGS. 2 to 6. The treatment method will be generally described with reference to FIG. 2. The treatment method includes a displacement step (step ST11) of changing a posture of a head H of the patient; an opening step (step ST12) of opening a mouth M of the patient; a laryngeal exposure step (step ST13) of exposing a larynx of the patient; an insertion step (step ST14) of inserting the medical appliance 100; and an indwelling step (step ST15) of indwelling the medical appliance 100 in a trachea T.

Note that prior to the execution of at least the insertion step in the method, the medical appliance 100 is attached to a tip end of a tube 400 to be inserted into the trachea T by using a thread or the like.

Figure 3:
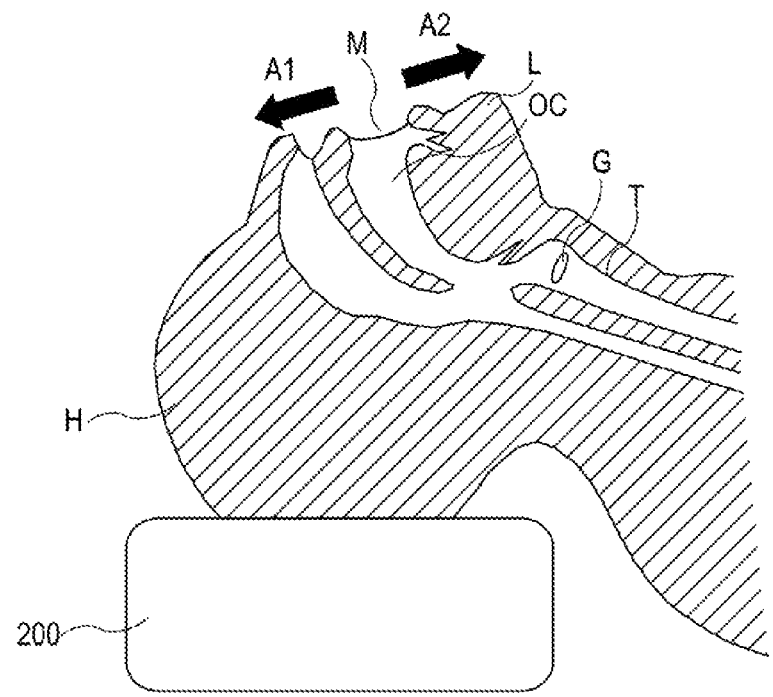
FIG. 3 is an explanatory diagram for illustrating a displacement step and an opening step in the abovementioned treatment method.

First, in the displacement step, for facilitating inserting the medical appliance 100 into the patient, a lower jaw L of the patient's head H is raised up as shown in FIG. 3 in such a manner that an angle formed between an oral cavity OC and the trachea T of the patient is set closer to 180 degrees as compared with a case where the patient is in a normal dorsal position (step ST11). A tool, for example, a pillow 200, can be used to help adjust positions of the oral cavity OC and the trachea T.

Next, in the opening step, the mouth M of the patient is kept in an open state by using hands and fingers of a doctor, etc. as indicated by arrows A1 and A2 in FIG. 3 (step ST12).

Figure 4:
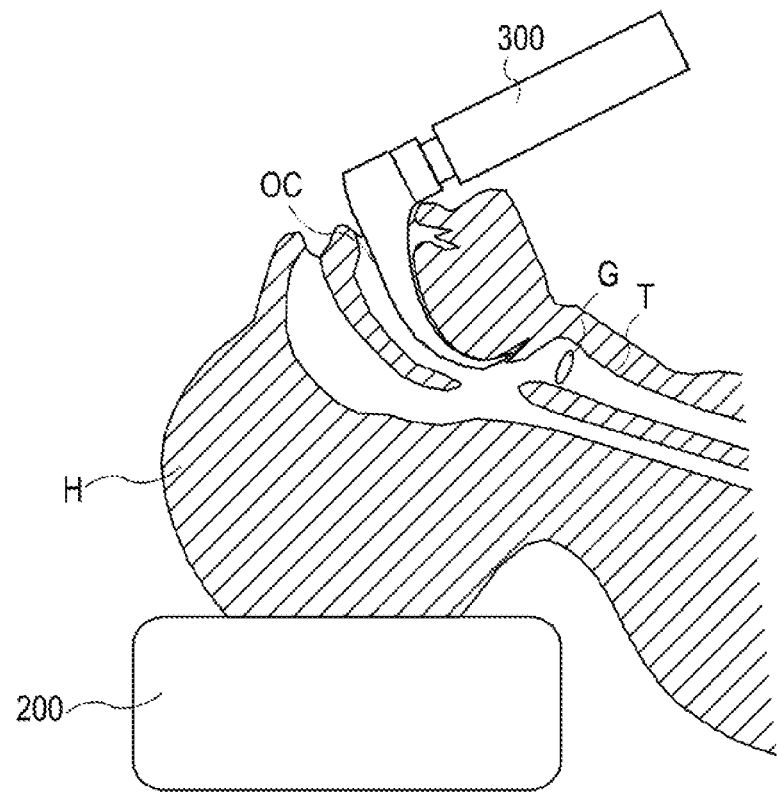
FIG. 4 is an explanatory diagram for illustrating a laryngeal exposure step in the abovementioned treatment method.
Figure 5:
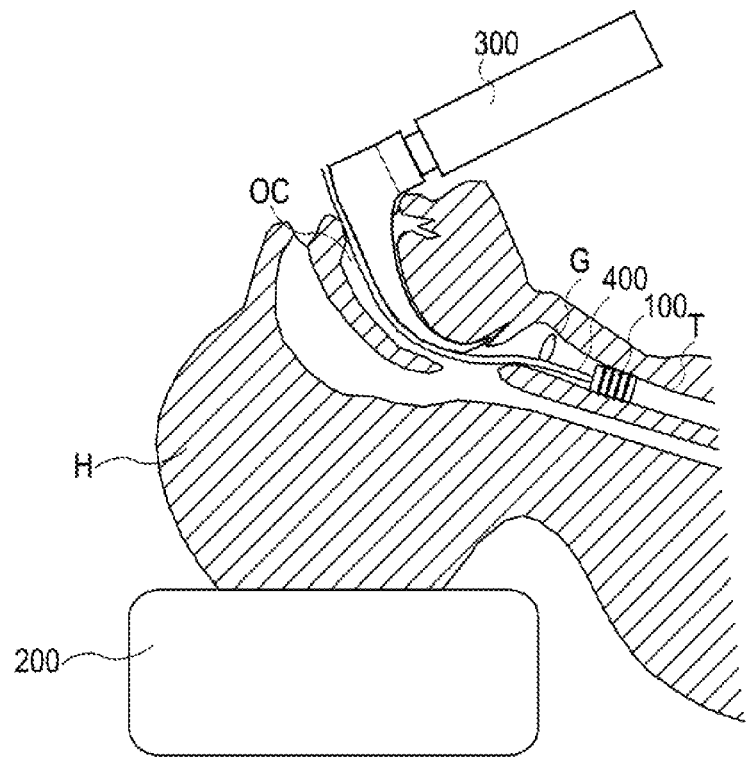
FIG. 5 is an explanatory diagram for illustrating an insertion step in the abovementioned treatment method.

Next, as shown in FIG. 4, a blade of a laryngoscope 300 is inserted into the oral cavity OC and moved toward a epiglottic vallecula, thereby exposing the larynx (step ST13). Upon catching sight of a glottis G, the tube 400 with the medical appliance 100 attached to the tip end thereof is inserted into the oral cavity OC, moved toward the glottis G, and inserted into the glottis G (step ST14).

When it can be confirmed that the medical appliance 100 has passed through the glottis G, the tube 400 is rotated in a circumferential direction, that is, twisted, thereby cutting off the thread that connects the tube 400 to the medical appliance 100 using the friction between the medical appliance 100 and the inner wall surface of the trachea T.

Figure 6:
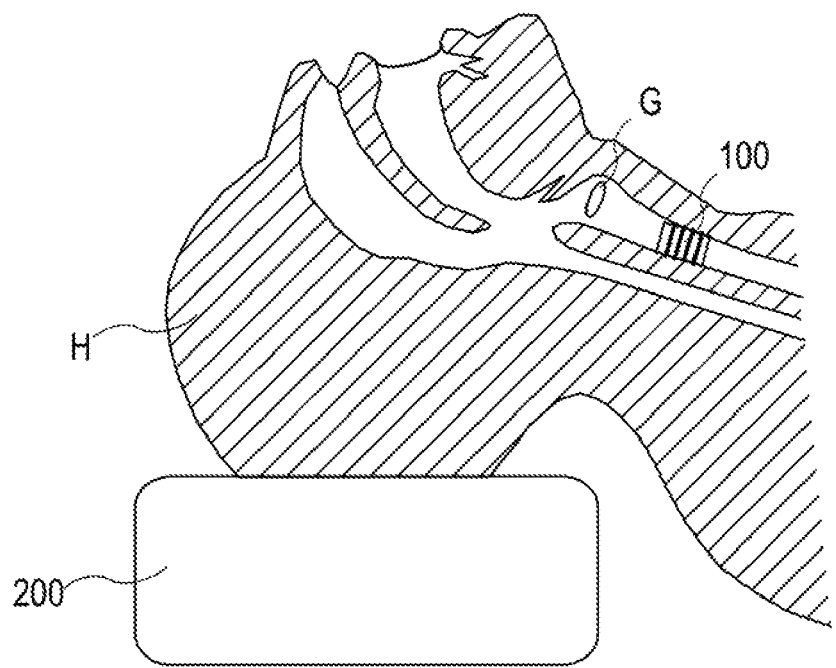
FIG. 6 is an explanatory diagram for illustrating an indwelling step in the abovementioned treatment method.

When the thread connecting the medical appliance 100 to the tube 400 has been cut off or separated, the tube 400 is pulled away from the trachea T and the laryngoscope 300 is pulled away from the oral cavity OC in a state where the medical appliance 100 has been indwelled in an upper portion of the trachea T as shown in FIG. 6 (step ST15). Alternatively, the medical appliance 100 may be indwelled in the trachea T in such a manner that a sheath is moved into the trachea T in a state where the medical appliance 100 has been accommodated in the sheath, and the medical appliance 100 is released or pushed out by a plunger or the like when the sheath arrives at a target site.

Functions and advantages will now be described. The treatment method is configured to execute the indwelling step of indwelling the medical appliance 100 in the trachea T of the patient, the medical appliance 100 having the metal rings 21 to 24 of the two types of metals disposed side by side on the side surface of the pipe body 10, and the medical appliance 100 is configured to generate the current between the adjacent metals of the metal rings 21 to 24 by the foreign substance or the saliva having flown into the trachea T. It is, therefore, possible to apply an electric stimulus to the trachea T and cause the patient to exhibit the cough reflex of encouraging the elimination of the foreign substance without the use of an instrument connected to a power supply or the like via a lead wire as required in the conventional technique.

Furthermore, the treatment method is configured to include the insertion step, prior to the indwelling step, of orally inserting the medical appliance 100. It is, therefore, possible to insert the medical appliance 100 from the oral cavity OC into the trachea T to indwell the medical appliance 100 in the trachea T without the need to perform incision or the like on the patient, and relatively alleviate the patient's burden.

Moreover, the treatment method is configured to execute the opening step, prior to the indwelling step, of opening the mouth M of the patient. It is, therefore, possible to insert the medical appliance 100 from the oral cavity OC into the trachea T to indwell the medical appliance in the trachea T, and relatively alleviate the patient's burden similarly to the above.

Furthermore, the treatment method is configured to include the displacement step, prior to the indwelling step, of raising up the lower jaw L of the patient in such a manner that the angle formed between the oral cavity OC and the trachea T of the patient is set greater than that in the normal dorsal position and closer to 180 degrees. It is, therefore, possible to smoothly insert the medical appliance 100 into the trachea T.

Moreover, the medical appliance 100 is configured to include the deformation portion 30 widening or constricting the pipe body 10 as the trachea T widens or constricts. It is, therefore, possible to prevent the medical appliance 100 from deviating from the predetermined position in the trachea T or keep the medical appliance 100 almost positional deviation free even when the trachea T widens by the respiration or the like. It is, therefore, possible to maintain the function of the medical appliance 100 of encouraging the cough reflex even when the trachea T widens or constricts by the respiration or the like.

Furthermore, the deformation portion 30 can be constituted by, for example, the plate springs attached to the inner wall surface of the pipe body 10 by the fusion bonding or the like.

Note that the present invention is not limited to the abovementioned embodiments and various modifications can be made of the present invention within the scope of the claims. The embodiments in which the metal rings 21 to 24 that constitute the current generation unit 20 are disposed on the outer wall surface of the pipe body 10 has been described above; however, the present invention is not limited to that embodiment. Alternatively, the metal rings 21 to 24 may be bonded to the inner wall surface of the pipe body 10 by the fusion bonding or the like as long as a weak current can be generated to encourage the cough reflex of the patient. Furthermore, the embodiment in which the plate springs that constitute the deformation portion 30 are bonded to the inner wall surface of the pipe body 10 by the fusion bonding or the like; however, the present invention is not limited to the embodiment. Alternatively, the plate springs may be bonded to the outer wall surface of the pipe body 10 by fusion bonding or the like in a state where the plate springs are rolled into a circular shape and biased to generate an elastic force for enabling the plate springs to widen radially outward.

Moreover, the embodiment in which the metal rings 21 to 24 of the current generation unit 20 are configured such that the adjacent metal rings are formed from the different materials, respectively has been described; however, the present invention is not limited to the embodiment. Alternatively or additionally, at least one pair of the adjacent metal rings, for example, only the metal rings 21 and 22 may be formed from the different materials as long as the weak current can be generated to encourage the cough reflex. Furthermore, members that constitute the current generation unit are not limited to the metal rings and the current generation unit may be configured such that a plurality of metals other than the metal rings is disposed side by side, obliquely or in a zigzag fashion with respect to an axis of the pipe body 10, i.e., the axial direction.

DESCRIPTION OF REFERENCE NUMERALS AND SIGNS 100 medical appliance,
10 pipe body,
20 current generation unit,
21-24 metal ring,
30 deformation portion,
31, 32 plate spring,
200 pillow,
300 laryngoscope,
400 tube,
A1, A2 direction of opening the mouth,
G glottis,
H head,
L lower jaw,
M mouth,
OC oral cavity,
T trachea.

What is claimed is:

1. A treatment method comprising:
   indwelling a medical appliance in a trachea of a patient, the medical appliance having a plurality of types of metals disposed on a side surface of a pipe body;
   while indwelling, the medical appliance generating a current between adjacent metals out of the plurality of types of metals when exposed to a foreign substance or saliva having flown into the trachea.

2. The treatment method according to claim 1, further comprising: prior to the indwelling, orally inserting the medical appliance.

3. The treatment method according to claim 2, further comprising: prior to the indwelling, opening a mouth of the patient.

4. The treatment method according to claim 3, further comprising: prior to the indwelling, changing a posture of a head of the patient by raising up a lower jaw.

5. The treatment method according to claim 1, further comprising: prior to the indwelling, opening a mouth of the patient.

6. The treatment method according to claim 5, further comprising: prior to the indwelling, changing a posture of a head of the patient by raising up a lower jaw.

7. The treatment method according to claim 1, further comprising: prior to the indwelling, changing a posture of a head of the patient by raising up a lower jaw.

8. A medical appliance comprising:
a pipe body that can be indwelled in a trachea of a patient; and
a current generation unit comprising:
a plurality of types of metals disposed side by side on a side surface of the pipe body, wherein a current is generated between adjacent metals out of the plurality of types of metals when exposed to a foreign substance or saliva having flown into the trachea.

9. The medical appliance according to claim 8, further comprising: a deformation portion widening or constricting the pipe body as the trachea widens or constricts.

10. The medical appliance according to claim 9, wherein the deformation portion includes a plate spring.

11. The medical appliance according to claim 10, wherein the pipe body is made from one or more of polyurethane, polyvinyl chloride, or silicone rubber.

12. The medical appliance according to claim 10, wherein the plurality of metals includes one or more of a cobalt chrome alloy or a nickel chrome alloy.

13. The medical appliance according to claim 8, wherein the current is a galvanic current.

14. A treatment method comprising:
inserting a medical appliance in a trachea of a patient, the medical appliance having a plurality of adjacent metals disposed on a side surface of a pipe body forming the medical appliance;
indwelling the medical appliance in the trachea; and
while indwelling, the medical appliance generating a current between the adjacent metals when exposed to a foreign substance or saliva having flown into the trachea.

15. The treatment method according to claim 14, wherein inserting the medical device comprises attaching the medical appliance to an end of a tube.

16. The treatment method according to claim 15, further comprising: raising a lower jaw of the patient to create an angle between an oral cavity and the trachea of the patient is substantially near 180 degrees.

17. The treatment method according to claim 16, wherein a pillow aids in raising the lower jaw.

18. The treatment method according to claim 17, wherein inserting the medical appliance further comprises: inserting a laryngoscope into the oral cavity to expose the larynx.

19. The treatment method according to claim 18, wherein inserting the medical appliance further comprises:
upon viewing a glottis, moving the tube past the glottis; and
inserting the medical appliance in the trachea.

20. The treatment method according to claim 19, further comprising: twisting the tube to detach the medical appliance in the trachea.

* * * * *